United States Patent [19]
Bates et al.

[11] Patent Number: 6,082,357
[45] Date of Patent: Jul. 4, 2000

[54] MECHANICAL VENTILATOR

[75] Inventors: Jason Hamilton Tunstall Bates, Brossard; Thomas Florian Schuessler, Montreal; Mohsen Ahmadi, St. Lambert, all of Canada

[73] Assignee: McGill University, Montreal, Canada

[21] Appl. No.: 09/047,210

[22] Filed: Mar. 25, 1998

[51] Int. Cl.[7] .................................................. A61M 16/00
[52] U.S. Cl. ............................. 128/204.18; 128/204.23; 128/204.24; 128/205.18
[58] Field of Search ....................... 128/204.18, 203.24, 128/204.22, 204.23, 204.24, 205.11, 205.18

[56] References Cited

U.S. PATENT DOCUMENTS

| | | | |
|---|---|---|---|
| 3,429,326 | 2/1969 | Arnell et al. | 128/204.24 |
| 3,739,775 | 6/1973 | Helm et al. | 128/204.24 |
| 3,957,047 | 5/1976 | Freytag et al. | 128/201.24 |

*Primary Examiner*—John G. Weiss
*Assistant Examiner*—V. Srivastava
*Attorney, Agent, or Firm*—Swabey Ogilvy Renault

[57] ABSTRACT

A mechanical ventilator for ventilating a patient employs an air displacement member mounted for oscillating motion in a chamber; preferably the chamber is semi-cylindrical and the air displacement member is a vane mounted for oscillating movement about an axis of rotation such that a free outer edge surface of the vane is maintained in closely spaced apart relationship with the interior wall of the chamber throughout the oscillating; the ventilator permits significant variation in the ventilation flow waveform.

12 Claims, 1 Drawing Sheet

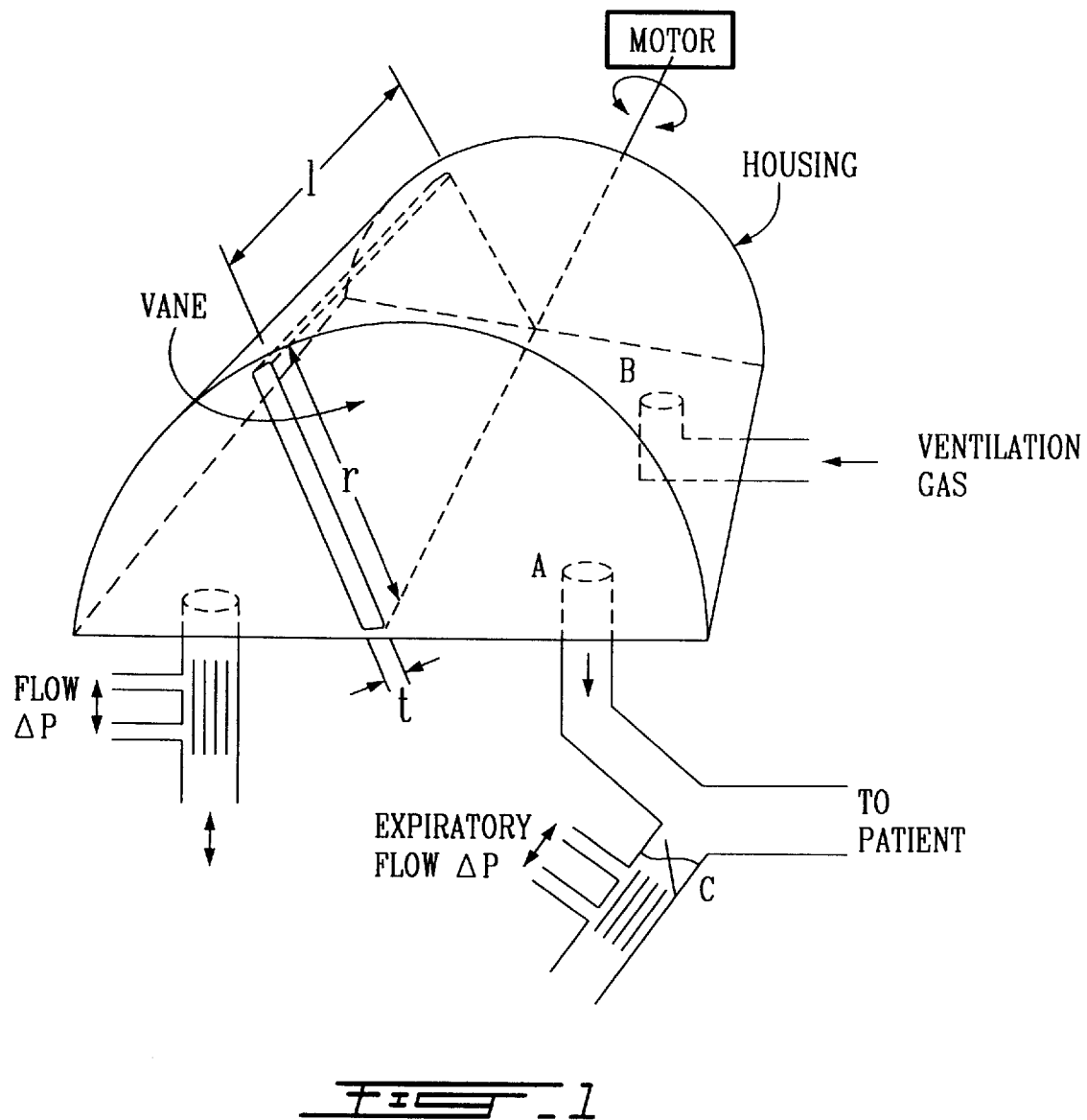
FIG_1

MECHANICAL VENTILATOR

BACKGROUND OF THE INVENTION

This invention relates to a ventilator and an improved ventilating method.

It is common for patients in the intensive care unit to be connected to mechanical ventilators to provide partial or complete assistance in breathing.

Weaning patients from ventilatory support is one of the major challenges involved in their case. The weaning process involves the application of an appropriate level of partial ventilatory support coupled with an ongoing assessment of the patient's status, so that the support level may be adjusted as necessary. For effective implementation this process requires that the mechanical properties of the patient's respiratory system be monitored regularly. With this information the magnitude of the muscular breathing efforts applied by the patient can be determined, and any adverse changes in the mechanical properties of the lungs can be determined.

The mechanical properties of the lungs are crucial determinants of their ability to function properly. Despite this, the assessment of respiratory mechanical function in mechanically ventilated patients in the intensive care unit is currently rudimentary, being limited for the most part to consideration of peak airway pressures and to visual inspection of flow-volume loops.

Many mechanical ventilators are available commercially. However, none is able to deliver both conventional ventilation flow waveforms and high frequency ventilation simultaneously. Also, although most modern ventilators have a variety of available flow waveforms they can deliver during inspiration, these are all pre-programmed and represent those considered the most important at the time of manufacture. No commercially available ventilator can deliver an arbitrary inspiratory flow waveform (within its band-width capabilities) with high precision.

Although some ventilators have the capability to estimate simple parameters of patient respiratory mechanics, there is a need for greater accuracy of signal measurement and greater sophistication in the analysis methods used.

SUMMARY OF THE INVENTION

In accordance with the invention there is provided a mechanical ventilator for human use which can be used both as a means of life-support in cases where the patient's respiratory musculature is unable to adequately ventilate the lungs, and as a means of applying broad-band oscillations in flow to the lungs for the purposes of identifying pulmonary mechanical parameters.

In accordance with one particular embodiment of the invention there is provided a mechanical ventilator comprising a hollow chamber having an interior wall, an air displacement member mounted for oscillating movement in said chamber, said air displacement member having first and second opposed air displacing faces, and a free outer surface between said faces, motor means to oscillate said displacement member in said chamber such that said free outer surface of said displacement member is maintained in closely spaced apart relationship with said interior wall throughout said oscillating movement, first and second variable zones defined in said chamber, said first zone being defined between said first face and said interior wall and said second zone being defined between said second face and said interior wall, and an air outlet and an air inlet in said first variable zone and an air flow port in said second variable zone for flow of air in and out of said second zone, and said closely spaced apart relationship being selected such that resistance to air flow between said free outer surface and said interior wall is greater than mechanical impedance of a patient receiving air discharged from said air outlet.

In accordance with another particular embodiment of the invention there is provided a mechanical ventilator comprising a hollow chamber having a semi-cylindrical interior wall, an air displacement vane mounted for oscillating radial motion in said chamber, said vane having a free outer edge surface in closely spaced apart relationship with said interior wall, said relationship being maintained throughout said oscillating radial motion, said oscillating motion having an air discharge mode and an air intake mode, an outlet for discharge of air from said chamber during said air discharge mode, and an air inlet for intake of air into said chamber during said air intake mode, said closely spaced apart relationship being selected such that the resistance to air flow between said free outer edge surface and said interior wall is greater than mechanical impedance of a patient receiving air discharged from said air outlet.

In accordance with still another embodiment of the invention there is provided in a method of ventilating a patient in which air is discharged from a ventilating chamber by oscillating motion of an air displacement member, the improvement wherein chamber parameters comprising the volume of air discharged from the chamber and air pressures within the chamber are monitored and pulmonary mechanical properties of the patient are assessed from said parameters.

In accordance with yet another embodiment of the invention there is provided a method of ventilating a patient comprising providing a hollow chamber having a semi-cylindrical interior wall, oscillating an air displacement vane in said chamber about an axis of rotation such that a free outer edge surface of said vane is maintained in closely spaced apart relationship with said interior wall throughout said oscillating, each oscillation cycle having sequentially an air discharge phase and an air intake phase, and discharging ventilating air to said patient in each air discharge phase.

DESCRIPTION OF PREFERRED EMBODIMENTS

The ventilator of the invention preferably includes valve means associated with said air outlet and air inlet, and control means adapted to maintain said air outlet open and said air inlet closed during an air discharge mode, and said air outlet closed and said air inlet open during an air intake mode.

The ventilator also preferably includes means to determine flow of air through the air flow port.

In an especially preferred embodiment the ventilator includes means for determining respiratory mechanical function from parameters of the chamber, said parameters comprising volume of air discharged from said first zone, air pressure in said first zone, pressure-flow characteristics of a conduit from said air outlet to the patient, and air pressure in the second zone or flow of air through the air flow port in the second zone.

The motor means which drives the air displacement member or vane suitably includes a control means for varying the frequency of the oscillating motion and the displacement of the air displacement member, the angular displacement in the case of the vane, during the oscillating motion.

Variation of the parameters of the oscillating motion alters the chamber parameters. Variation of the chamber parameters provokes response from the patient which permits assessment of lung function.

Thus the ventilator has a high band-width capability; that is, it can deliver flow waveforms to the lung with frequencies up to 10 Hz or more as well as being able to deliver conventional waveforms at normal breathing frequencies. Also, the ventilator is completely flexible in the waveforms that it can deliver, due to its being entirely under computer control.

Finally, the ventilator is designed so that the mechanical impedance of the load being ventilated (i.e. the patient) is identified continuously without the need for additional measuring equipment having to be installed in the ventilator circuit.

BRIEF DESCRIPTION OF DRAWINGS

FIG. 1 illustrates schematically a ventilator of the invention in a preferred embodiment.

DESCRIPTION WITH REFERENCE TO DRAWINGS

The basic design of the ventilator is shown in FIG. 1. It consists of a half-cylindrical housing (inside radius r, length l) enclosed at both ends and on the bottom by flat plates. Pivoting inside the housing along an axis at its centre of curvature is a vane. The rod about which the vane pivots passes through the two housing endplates via sealed bearings.

The vane is machined to have dimensions r–d and l–d, where d is a very small quantity (small fraction of a mm). The dimensions r and 1, on the other hand have dimensions such that the vane is able to displace a liter or more of gas as it rotates throughout its allowable range. In other words, the vane has essentially the same dimensions as the inside of the housing except that it does not actually touch the walls of the housing as it rotates. The vane is driven by an electric torque motor with power sufficient to oscillate the vane. By way of example the vane may oscillate at frequencies up to 10 Hz and displacements at 10 Hz of up to 20 ml.

The floor of the housing to the right of the vane contains two valves, labelled in FIG. 1 as A and B. Valve A connects the housing directly to the patient via a relatively short segment of flexible but non compliant tubing. Thus, when A is open and B is closed, gas is forced into the patient's lungs as the vane sweeps in a clockwise direction (as seen from FIG. 1). Conversely, when A is closed and B is open, fresh air is drawn into the housing as the vane sweeps in a counter clockwise direction. At the same time, a third valve (labelled C in FIG. 1) allows the patient to exhale directly to atmosphere through a conventional pneumotachograph.

In the floor of the housing to the left of the vane is another hole which connects to atmosphere through a conventional pneumotachograph. A differential pressure transducer connected across the two ports of the pneumotachograph measures gas flow as it enters and leaves the housing from the left side of the vane.

This design allows the patient to be ventilated effectively, provided the dimensions of the housing are chosen correctly, the motor has sufficient power to overcome the inertia of the vane and the mechanical impedance of the patient, and the clearance between the vane and housing is sufficiently small that most of the vane displacement results in gas moving into the patient rather than flowing back past the vane. This latter requirement, broadly speaking, means that the resistance to gas flow of the space between the vane and the housing must be large compared to that of the patient.

This design also, however, allows one to estimate the mechanical load being ventilated. The angular displacement of the vane is accurately measured, and can be converted into volume displacement of the vane (V) from the geometry of the system (the housing and vane are constructed of essentially perfectly rigid materials). This volume displacement has three components: volume displaced into the patient (Vpat), compressed volume in the housing (Vcomp), and volume loss due to back flow past the vane (Vback). Vcomp is obtained from the pressure measured inside the right housing and the volume of gas in it (again obtained from the angular position of the vane). Vback is obtained from the difference in the volume displacement of the vane and the integrated flow measured entering the left housing.

$$Vpat = V - Vcomp - Vback$$

The pressure required to drive Vpat into the patient through the ventilator tubing is the pressure (P) inside the right housing. From the pressure-flow characteristics of the ventilator tubing the pressure at the patient from P and the flow through the tubing (dvpat/dt) can be determined.

The key points of difference between the ventilator of the invention and existing ventilators are:

1) The ventilator is completely flexible. Any volume perturbation can be applied to the lungs; it is merely a matter of creating the waveform in software. No other device exists for such a purpose.
2) The ventilator provides measurements of patient respiratory mechanics without requiring the direct measurement of flow into the lungs, and requires no extra measuring equipment to be installed in the ventilation line. Furthermore, the ventilator will be able to assess patient mechanics more accurately than existing devices, and will be able to apply more sophisticated analysis methods.
3) The ventilator combines both conventional mechanical ventilation (for life support) and flexible volume oscillation capabilities (for respiratory mechanics testing) in a single device. No other device does this.
4) The ventilator in a particular embodiment is based on a novel rotating vane design that is compact and allows precision control of flow to the patient.

Thus the ventilator of the invention allows measurement of respiratory mechanics in patients, especially ICU patients. In a specific embodiment the ventilator is based around a vane that rotates inside a semi-circular housing. The vane is machined to have a finite but tiny clearance from the housing as it rotates through its allowable range, displacing up to 1.8 liters of gas into the patient. The vane is driven under full computer control by an electric torque motor capable of oscillating it throughout its range of movement at normal breathing frequencies, and of generating displacements at 10 Hz of up to 20 ml. This design allows the patient to be ventilated using conventional ventilator waveform. It also permits the estimation of the mechanical load being ventilated from measurements of the angular displacement of the vane and the pressures within the housing either side of the vane, obviating the need for direct measurement of flow. The new ventilator may serve as a flexible research tool for mechanics studies in ICU patients, and ultimately as a device for routine assessment of respiratory mechanical status.

The ventilator can be used in a hospital intensive care unit, and has application for patients being mechanically ventilated during surgery.

We claim:

1. A mechanical ventilator comprising a hollow chamber having an interior wall, an air displacement member mounted for oscillating movement in said chamber, said air displacement member having first and second opposed air displacing faces, and a free outer surface between said faces, motor means to oscillate said displacement member in said chamber such that said free outer surface of said displacement member is maintained in closely spaced apart relationship with said interior wall throughout said oscillating movement, first and second variable zones defined in said chamber, said first zone being defined between said first face and said interior wall and said second zone being defined between said second face and said interior wall, and an air outlet and an air inlet in said first variable zone and an air flow port in said second variable zone for flow of air in and out of said second zone, and said closely spaced apart relationship being selected such that resistance to air flow between said free outer surface and said interior wall is greater than mechanical impedance of a patient receiving air discharged from said air outlet.

2. A ventilator according to claim 1 further including valve means associated with said air outlet and air inlet, and control means adapted to maintain said air outlet open and said air inlet closed during an air discharge mode, and said air outlet closed and said air inlet open during an air intake mode.

3. A ventilator according to claim 1, including means to determine flow of air through said air flow port.

4. A ventilator according to claim 2, including means to determine flow of air through said air flow port.

5. A ventilator according to claim 3 including means for determining respiratory mechanical function from parameters of the chamber, said parameters comprising volume of air discharged from said first zone, air pressure in said first zone, pressure flow characteristics of a conduit from said air outlet to the patient, and air pressure in the second zone or flow through said air flow port.

6. A ventilator according to claim 4, including means for determining respiratory mechanical function from parameters of the chamber, said parameters comprising volume of air discharged from said first zone, air pressure in said first zone, pressure flow characteristics of a conduit from said air outlet to the patient, and air pressure in the second zone or flow through said air flow port.

7. A mechanical ventilator comprising a hollow chamber having a semi-cylindrical interior wall, an air displacement vane mounted for oscillating radial motion in said chamber, said vane having a free outer edge surface in closely spaced apart relationship with said interior wall, said relationship being maintained throughout said oscillating radial motion, said oscillating motion having an air discharge mode and an air intake mode, an outlet for discharge of air from said chamber during said air discharge mode, and an air inlet for intake of air into said chamber during said air intake mode, said closely spaced apart relationship being selected such that the resistance to air flow between said free outer edge surface and said interior wall is greater than mechanical impedance of a patient receiving air discharged from said air outlet.

8. A ventilator according to claim 7 further including motor means to drive said vane in said oscillating motion, and motor control means to vary the frequency of the oscillating motion and the angular displacement of said vane during said oscillating motion.

9. In a method of ventilating a patient in which air is discharged from a ventilating chamber by oscillating motion of an air displacement member, the improvement wherein chamber parameters comprising the volume of air discharged from the chamber and air pressures within the chamber are monitored and pulmonary mechanical properties of the patient are assessed from said parameters.

10. A method according to claim 9 wherein parameters of said oscillating motion are varied to alter said chamber parameters.

11. A method of ventilating a patient comprising providing a hollow chamber having a semi-cylindrical interior wall, oscillating an air displacement vane in said chamber about an axis of rotation such that a free outer edge surface of said vane is maintained in closely spaced apart relationship with said interior wall throughout said oscillating, each oscillation cycle having sequentially an air discharge phase and an air intake phase, and discharging ventilating air to said patient in each air discharge phase.

12. A method according to claim 11 including varying said oscillating, determining the volume of air discharged in said air discharge phase and the pressure in the chamber during said air discharge phase and assessing pulmonary mechanical properties of the patient from said volume and pressure.

* * * * *